United States Patent [19]

Buckman, Jr. et al.

[11] Patent Number: 5,484,391
[45] Date of Patent: Jan. 16, 1996

[54] DIRECT MANUAL CARDIAC COMPRESSION METHOD

[76] Inventors: Robert F. Buckman, Jr., 125 Chew La., Radnor, Pa. 19087; Michael M. Badellino, 213 Grown Lane Ter., Hatboro, Pa. 19040

[21] Appl. No.: 182,906

[22] Filed: Jan. 14, 1994

Related U.S. Application Data

[62] Division of Ser. No. 922,714, Jul. 30, 1992, abandoned.

[51] Int. Cl.$^6$ .................................................. A61H 1/00
[52] U.S. Cl. .......................... 601/135; 601/107; 601/153; 601/41; 128/639
[58] Field of Search .......................... 601/15, 41, 84, 601/107, 133, 134, 135, 85, 97, 148–153; 600/16; 128/419 P, 419 PG, 419 G, 419 D, 634, 642, 632, 633, 784, 639

[56] References Cited

U.S. PATENT DOCUMENTS

| | | |
|---|---|---|
| 1,242,806 | 10/1917 | Hohein . |
| 2,826,193 | 3/1958 | Vineberg . |
| 2,912,976 | 11/1959 | Grund . |
| 3,371,662 | 3/1968 | Heid et al. . |
| 3,389,703 | 2/1966 | Criswell et al. ...................... 128/419 D |
| 3,455,298 | 7/1969 | Anstadt . |
| 3,496,932 | 2/1970 | Prisk et al. . |
| 3,587,567 | 6/1971 | Schiff . |
| 3,613,672 | 10/1971 | Schiff . |
| 3,747,594 | 7/1973 | Bishop . |
| 4,048,990 | 9/1977 | Goetz . |
| 4,192,293 | 3/1980 | Asrican . |
| 4,448,190 | 5/1984 | Freeman ................................. 601/134 |
| 4,508,107 | 4/1985 | Strom et al. . |
| 4,536,893 | 8/1985 | Parravicini . |
| 4,690,134 | 9/1987 | Snyders . |
| 4,731,076 | 3/1988 | Noon et al. . |

(List continued on next page.)

FOREIGN PATENT DOCUMENTS 256694 7/1947 Switzerland .

OTHER PUBLICATIONS

"Mechanical Cardiac Actuation Achieves Hemodynamics Similar to Cardiopulmonary Bypass", Mark. P. Anstadt, M.D., et al., Surgery, vol. 108, No. 2, pp. 442–451, Aug. 1990.

"Pulsatile Reperfusion After Cardiac Arrest Improves Neurologic Outcome", Mark P. Anstadt, M.D., et al., Ann. Surg., vol. 214, No. 4, pp. 478–490, Oct. 1991.

"Direct Mechanical Ventricular Actuation For Cardiac Arrest in Humans–A Clinical Feasibility Trial", Mark P. Anstadt, M.D., et al., Chest, vol. 100, No. 1, pp. 86–92, Jul. 1991.

"Experimental And Clinical Evaluations Of Mechanical Ventricular Assistance", David B. Skinner, M.D., The American Journal of Cardiology, vol. 27, pp. 146–154, Feb. 1971.

"Direct Mechanical Ventricular Assistance–Acute And Long–Term Effects in the Dog", Capt. Philip S. Coogan, MC, USAF, et al., Arch Path, vol. 87, pp. 423–431, Apr. 1969.

Cohen, et al., *Circulation* 84 (4) II–9, Abstr. 0033, Oct. 1991.

Cohen, et al., *Journal of the American Medical Association*, vol. 267, No. 21, 2916–2923 Jun. 3, 1992.

*Primary Examiner*—Robert A. Hafer
*Assistant Examiner*—David J. Kenealy
*Attorney, Agent, or Firm*—Seidel Gonda Lavorgna & Monaco

[57] ABSTRACT

Methods for employing a heart massager for substernal heart massage are disclosed. The heart massager comprises a heart-contacting member connected to a handle. The disclosed method comprises the following steps: making an incision in the skin in an intercostal space; surgically separating the intercostal space; inserting the heart massager through the intercostal space and guiding heart-contacting member of the massager onto the ventricular region of the heart; and periodically pressing and releasing the handle so that the heart's ventricles are compressed and allowed to return to their non-compressed condition.

40 Claims, 9 Drawing Sheets

U.S. PATENT DOCUMENTS

| | | |
|---|---|---|
| 4,747,396 | 5/1988 | Richardson et al. . |
| 4,753,226 | 6/1988 | Zheng et al. . |
| 4,915,095 | 4/1990 | Chun . |
| 4,934,360 | 6/1990 | Heilbron et al. . |
| 4,962,758 | 10/1990 | Lasner et al. . |
| 5,224,469 | 7/1993 | Mocny . |

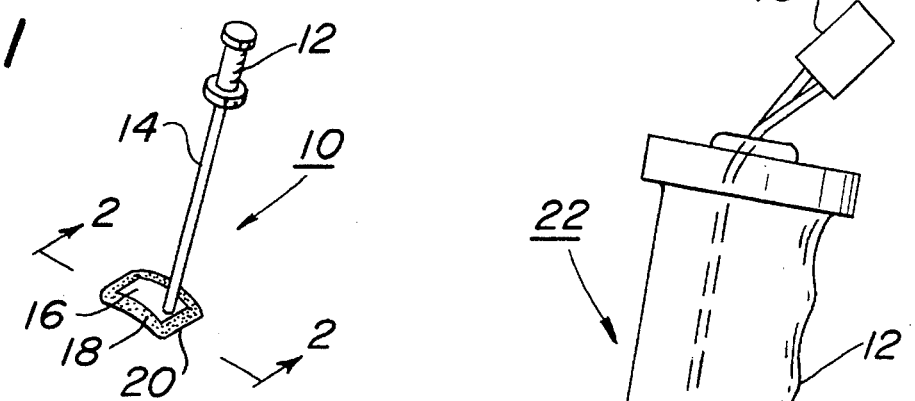
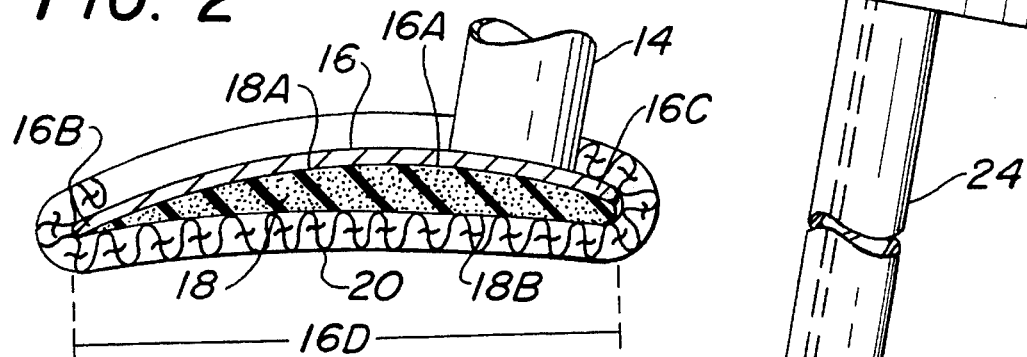
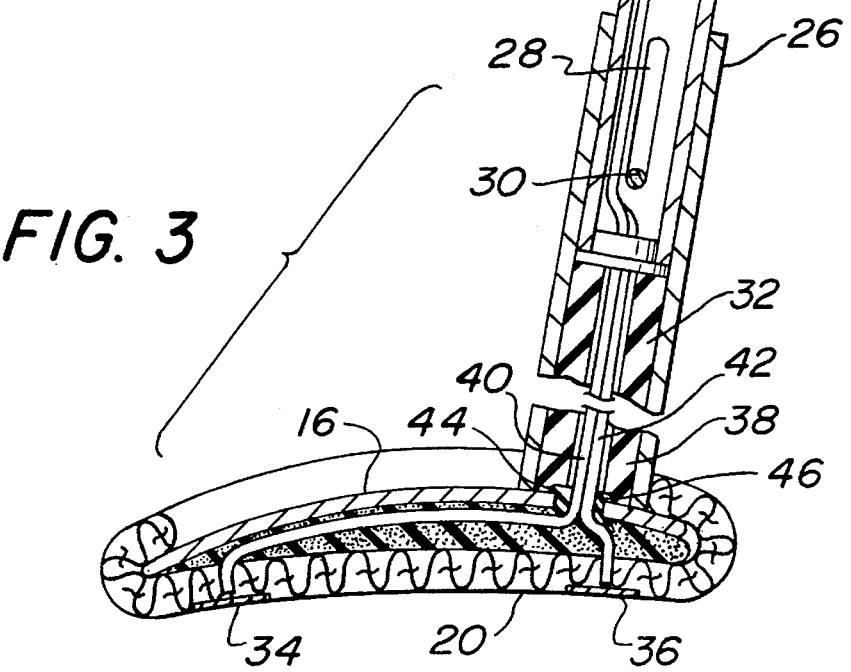

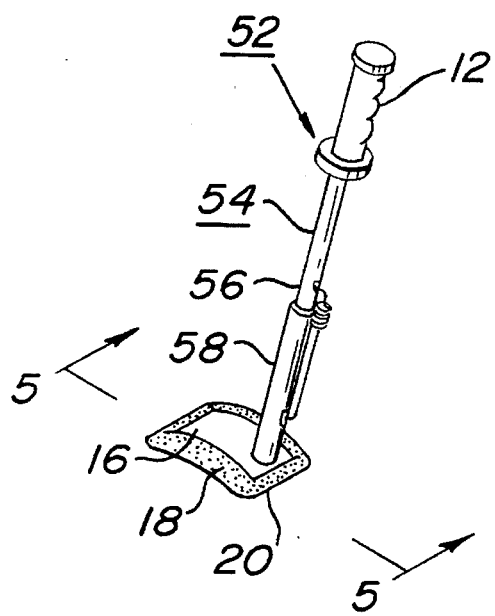
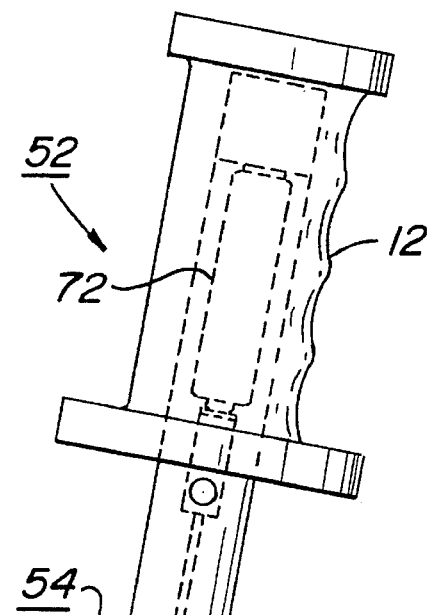
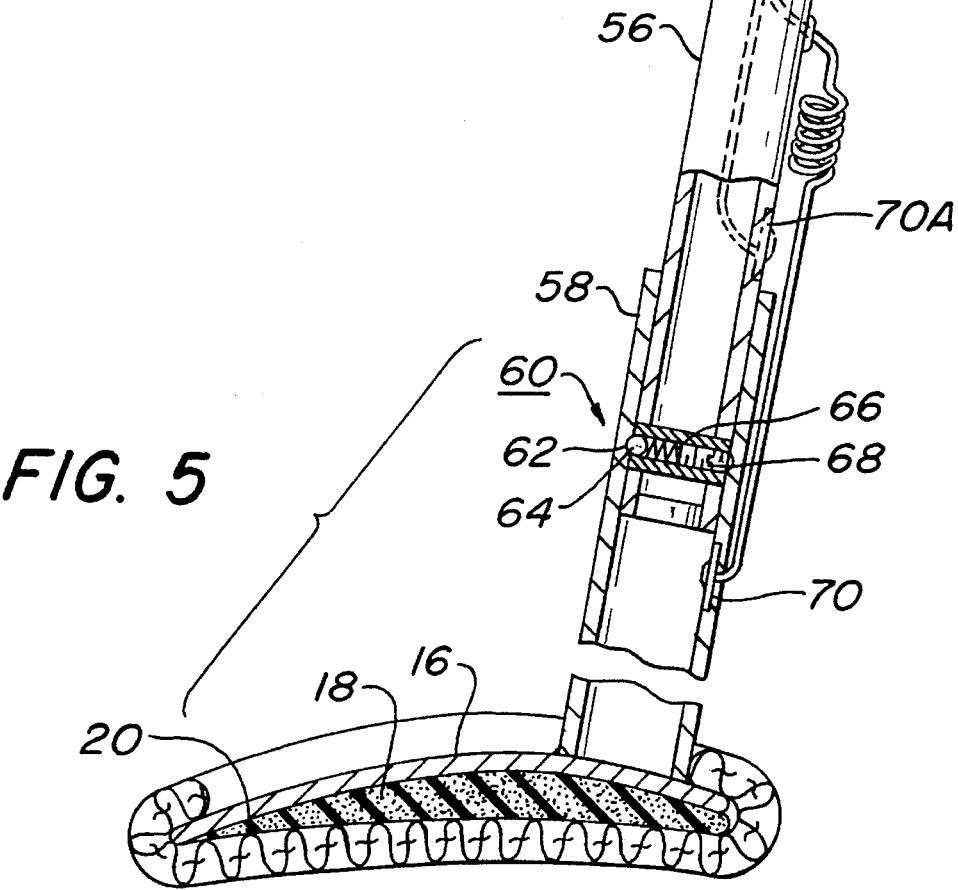
FIG. 4
FIG. 5

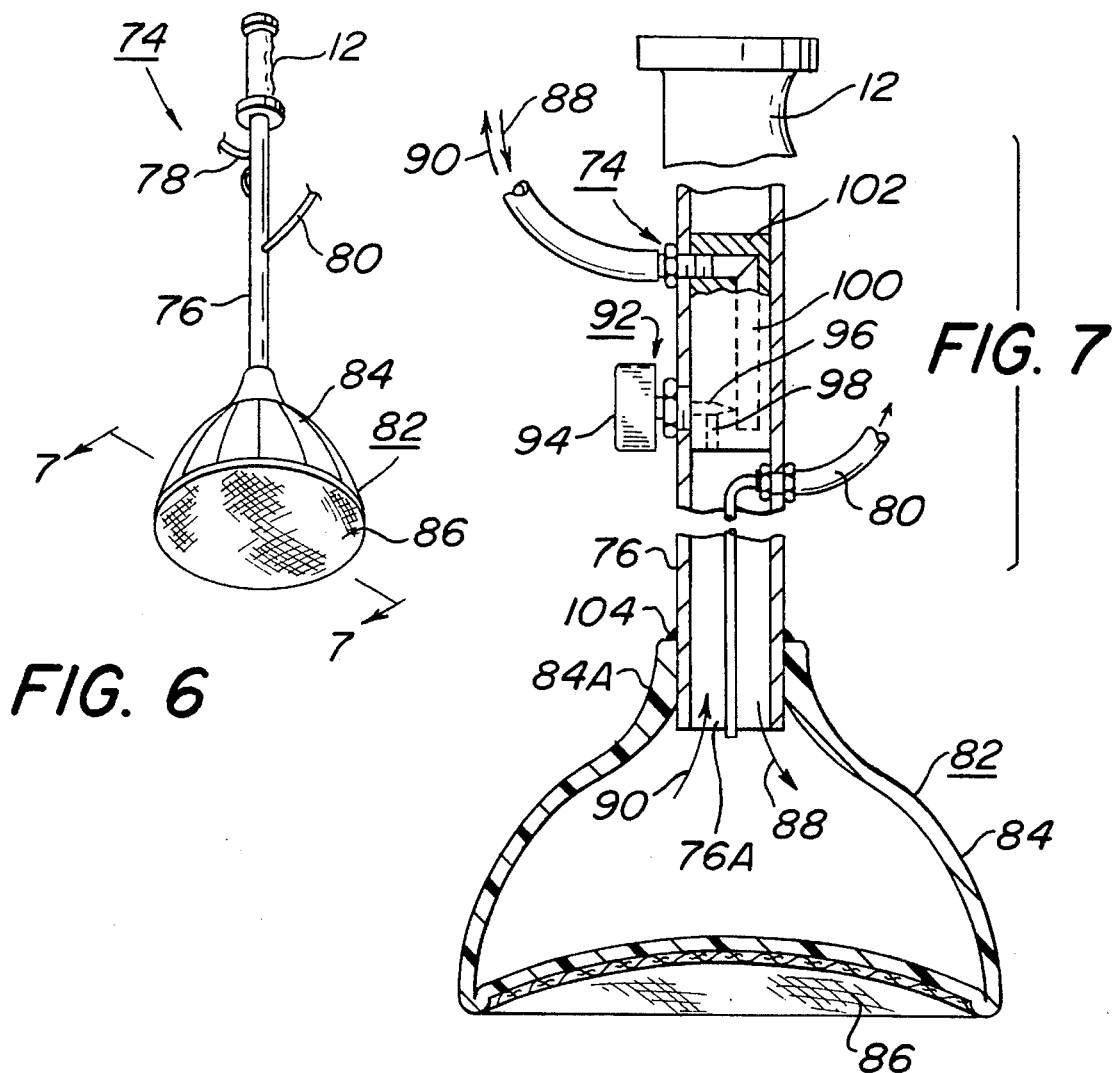
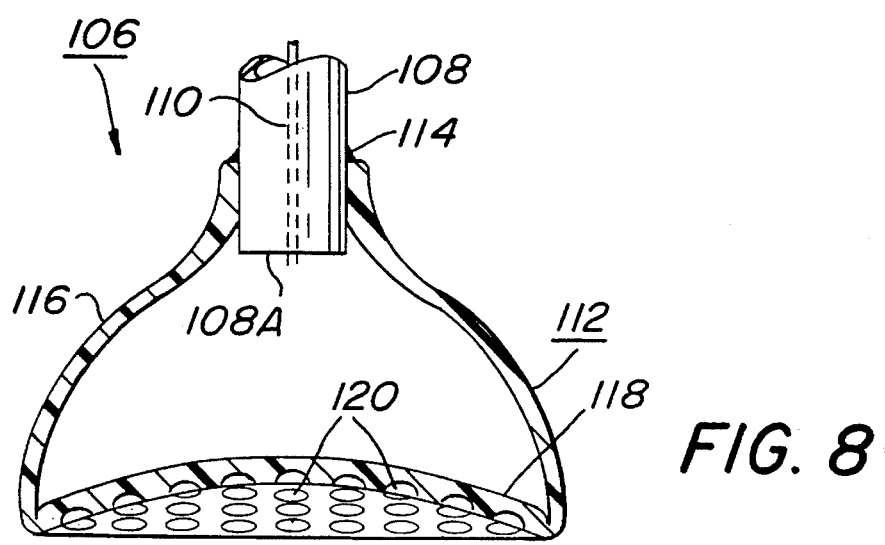

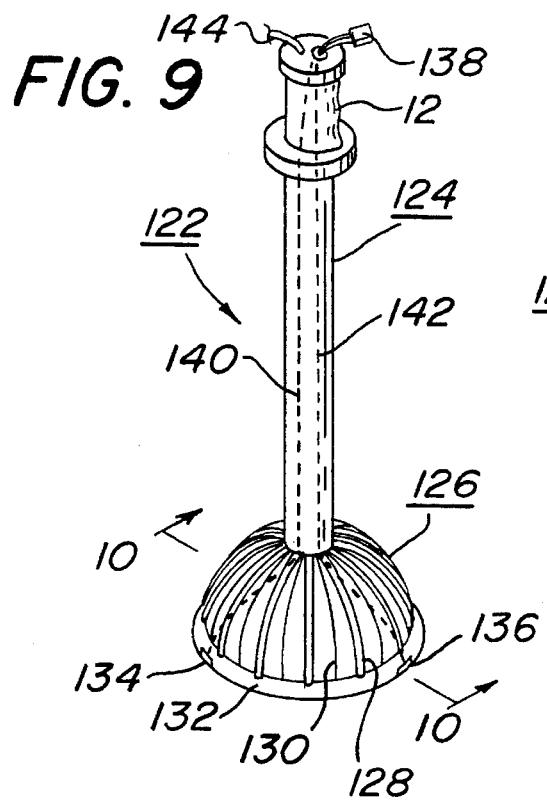
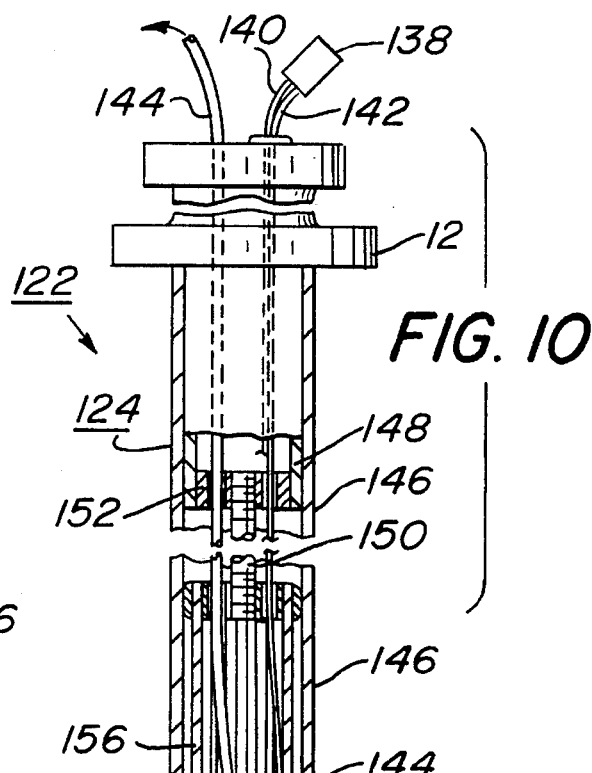
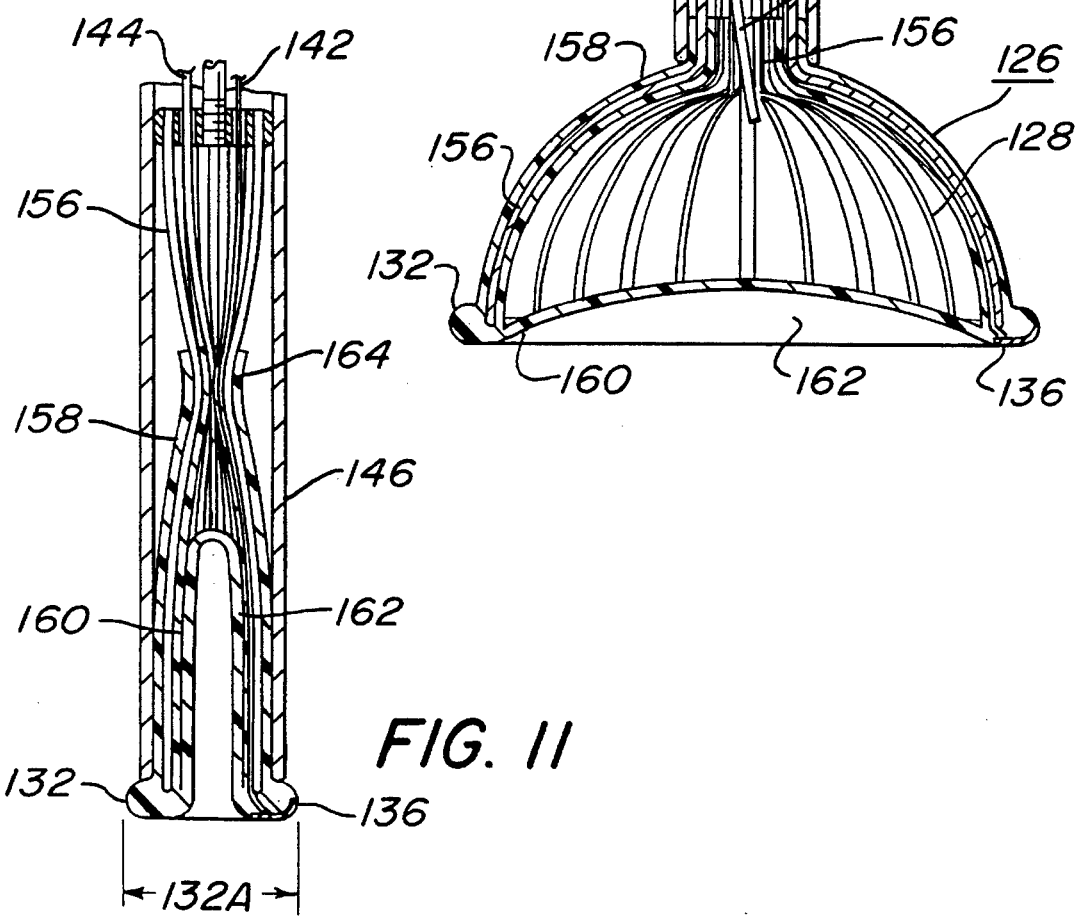

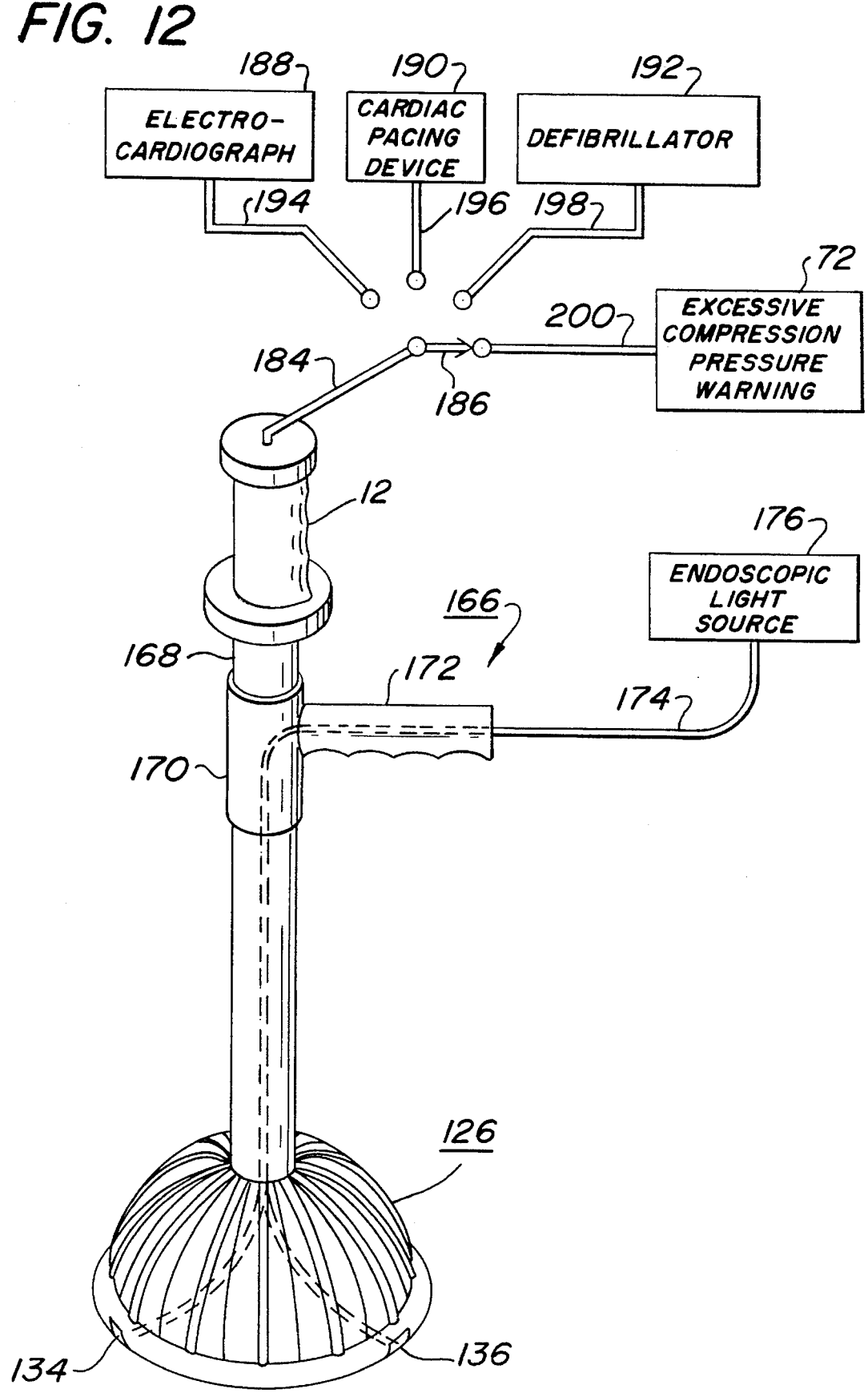

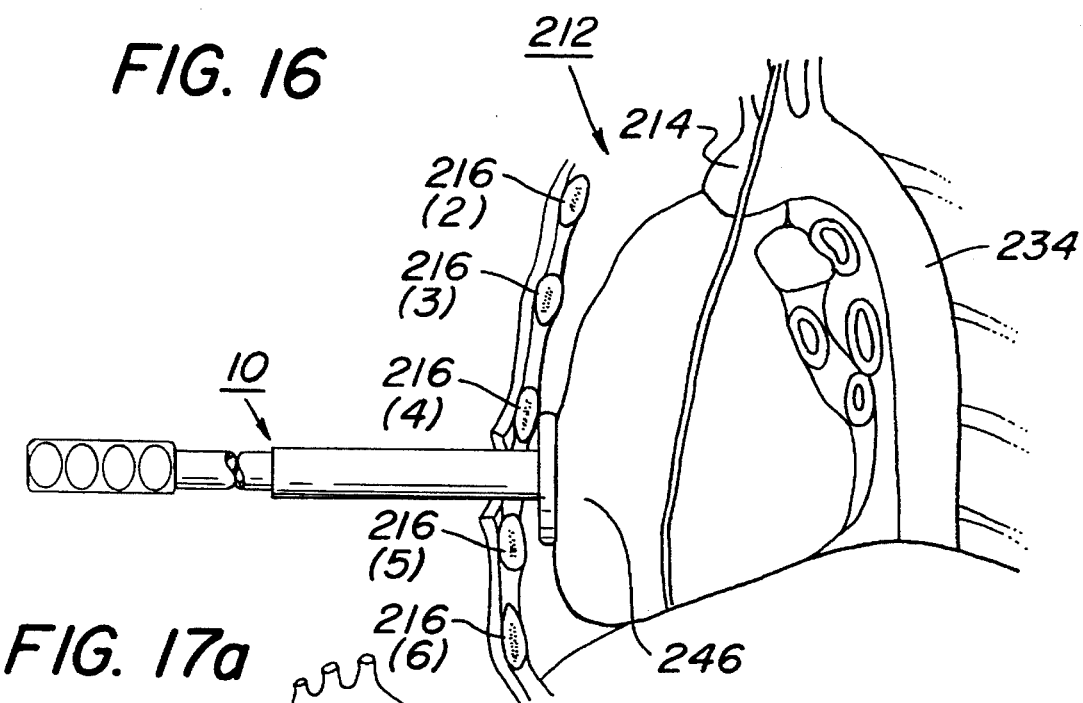
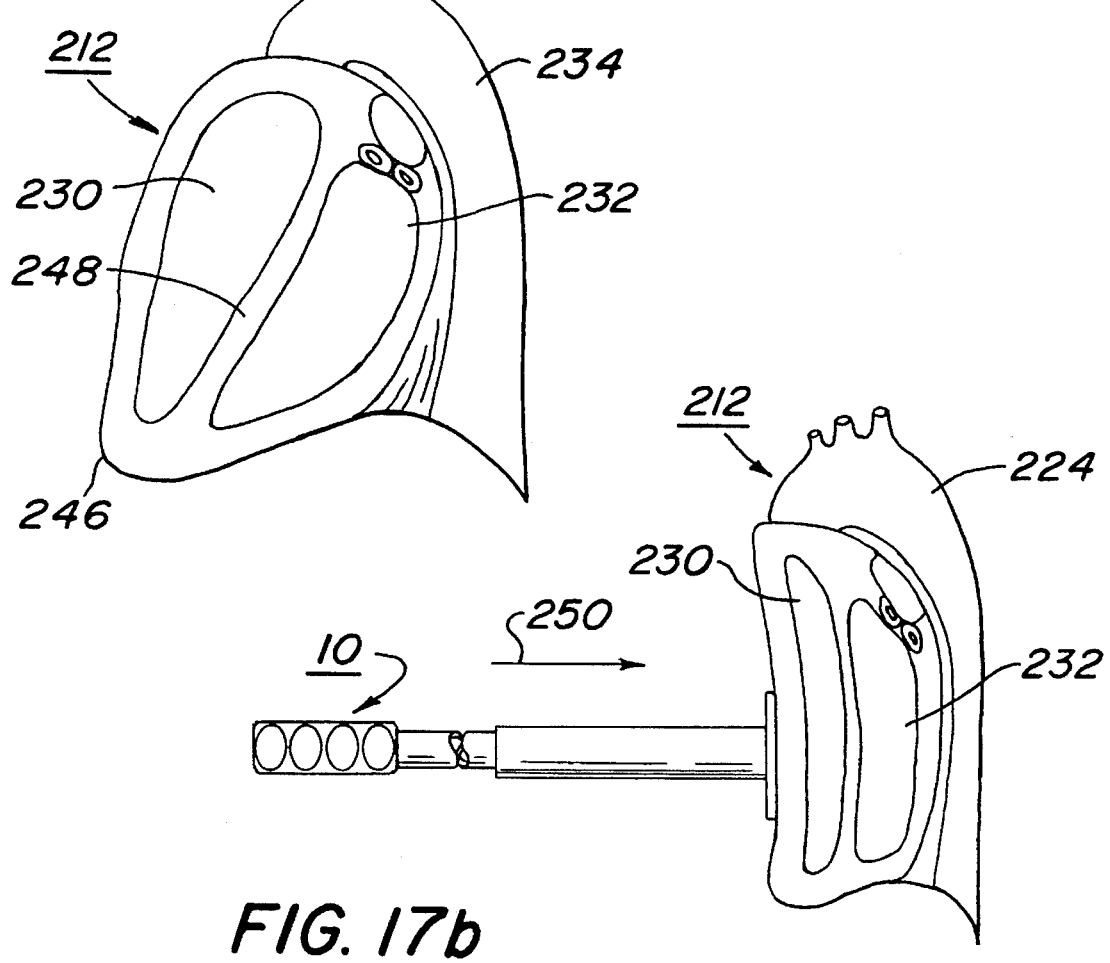

FIG. 18a
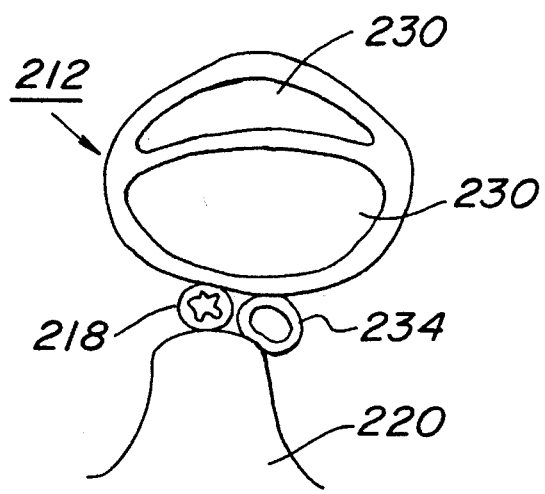
FIG. 18b
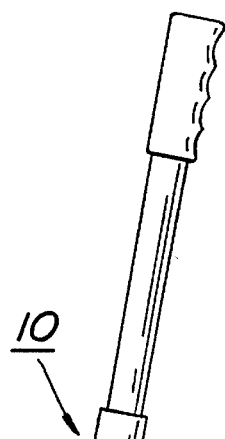
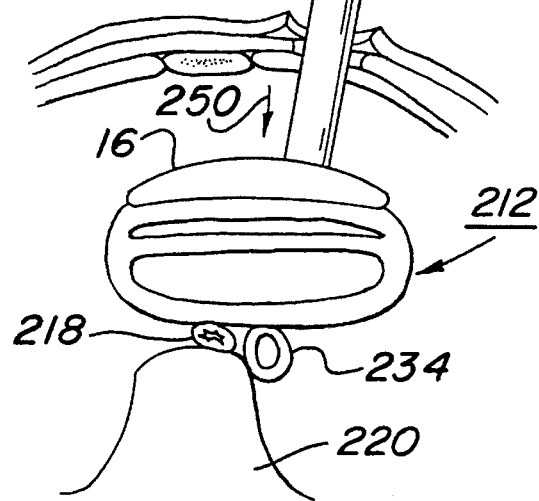
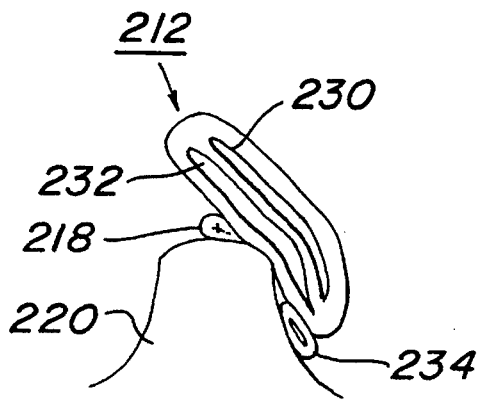
FIG. 18c

DIRECT MANUAL CARDIAC COMPRESSION METHOD

This is a divisional of application Ser. No. 07/922,714 filed on Jul. 30, 1992 abandoned.

FIELD OF THE INVENTION

The present invention relates to heart massagers and a method of use thereof and, more particularly, to various heart massagers each of which is introduced through a relatively small surgical incision made in the chest wall so that the massagers may be positioned to directly massage the heart during cardiac arrest.

BACKGROUND OF THE INVENTION

In the medical profession it is recognized that it is necessary, in the event of a cardiac arrest, to assist the heart in its pumping function until effective spontaneous cardiac contraction can restore normal blood circulation. During cardiac arrest, the pumping action of the heart ceases and blood flow stops. If blood flow or circulation is not sustained or reinstituted, either by restoration of spontaneous cardiac activity or by some other provision of artificial circulatory support, irreversible vital organ damage and clinical death will ensue.

Currently, several method are employed to sustain circulation during cardiac arrest. These methods include closed chest external and open chest internal cardio-pulmonary resuscitation (CPR) techniques. All of the external CPR techniques, as well as the devices which are used therewith, rely on depressing the sternum producing a generalized increase in intrathoracic pressure. This produces a low level of blood flow to the organs of the body. However, none of these external CPR devices nor their related techniques, develop enough direct mechanical compression of the ventricular chambers of the heart to produce physiologically significant blood flow. Open-chest, bi-manual cardiac compression, in which the heart is directly compressed by the hands of the operator, produces far more blood flow than any method of closed chest CPR. It is capable of supplying vital organs with more blood and produces a higher probability of survival than any method of closed chest CPR. During open-chest, internal CPR, an anterior-lateral chest incision is commonly used with the surgical incision being large enough to accommodate introduction into the chest cavity of both hands of an operator, so that a manual compression of the heart muscle may take place.

Both the external (closed chest) CPR and open chest techniques can be performed manually or with the aid of mechanical devices. With either technique, the goal is to maintain artificial circulation, including circulation through the heart itself, until spontaneous cardiac activity can be restored. This restoration almost always involves electrical defibrillation of the heart in which a direct current shock is administered to the heart muscle to restore its spontaneous contraction.

A method of performing internal CPR is described in U.S. Pat. No. 3,496,932 of Prisk et al. issued Feb. 24, 1970. This described method uses a small surgical incision, about one (1) inch, to accommodate the placement of a direct mechanical compression device on the heart muscle. The compression device comprises a generally cone-shaped plastic film serving as an inflatable and deflatable bladder which is connected to an air supplying stem which, in turn, is attached to an external pneumatic apparatus.

In the method of the '932 patent, a surgical incision is made in the upper abdomen below the lower tip (xiphoid) of the sternum for the purpose of introducing the device which is placed behind the sternum onto the heart. Before such an introduction, a trocar carrying a large tube and having a pointed tip is inserted into the incision, in an upward manner, into the space between the sternum and the anterior aspect of the pericardium, or alternatively into the pericardial sac itself. Entrance of this device carrying a sharp tip between the posterior aspect of the sternum and anterior aspect of the heart involves risk of accidently wounding the heart. After insertion, the tip of the trocar is moved until the desired location for the later placement of the inflatable/deflatable bladder on the heart is reached. Then, the trocar is withdrawn but the large tube carried by the trocar remains, allowing for the bladder to be inserted through the tube and onto the heart ready for periodic pneumatic inflation and deflation cycles of the bladder. These cycles are accomplished with the assistance of a mechanical pump apparatus to produce corresponding compression/relaxation cycles of the heart muscle to produce an artificial circulation during cardiac arrest.

Although the '932 patent may advantageously accomplish mechanical compression/relaxation of the heart by means of a small surgical incision so as to avoid an open-chest procedure, it is desired that such compression/relaxation be accomplished by a self-contained heart massager device having no reliance on any external mechanical device. Moreover, it is desired that a heart massager be positioned on the heart without the need for any sharp probing tip that might damage contacting elements of the body because of inadvertent contact therewith. Further, it is desired that the heart massager not only be devoid of a pointed tip but also have relatively small dimensions for insertion into the chest and a contoured surface for mating with the heart. Still further, it is desired that a heart massager be provided having collapsible features so as to minimize the size of the surgical incision needed for the introduction of the massager into the chest.

It is further desired that a method for inserting the heart massager be provided so that a surgical incision is not made through the abdomen.

It is still further desired, that means be provided to allow the heart massager to be guided to not only its most desirable/optimum position on the heart, but also be monitored and maintained at such a position during the direct mechanical compression of the heart muscle. Moreover, it is desired that the heart massager be provided with means to allow the massager to be re-positioned during use so that an optimum hemodynamic compression of the heart muscle and maximal blood flow to vital organs may be obtained during the massage and until spontaneous cardiac action can be restored.

Further, it is desired that the heart massager have provisions to accommodate direct cardiac defibrillation, detection of any abnormal electrocardiograph rhythm that might occur during the heart massage, and means for stabilizing any irregular heartbeats that might occur during the cardiac arrest condition.

Accordingly, it is an object of the present invention to provide a massager having no reliance on any external mechanical device apart from the massager per se to accomplish a direct massage of the heart muscle.

Another object of the present invention is to provide a heart massage that is not only devoid of a sharp tip that may unnecessarily and inadvertently damage body elements but also has relatively small dimensions and a contoured surface for mating with the heart.

It is a further object of the present invention to provide a massager having collapsible features so as to hold to a minimum the size of the surgical incision needed for the subcutaneous introduction of the massager onto the heart.

Still further it is an object of the present invention to provide a device having provisions for endoscopic (optical) guidance means so as to allow the massager to be initial positioned on the heart as desired to perform the massage, to be maintained at that initial position or to be repositioned during the massage so as to accomplish hemodynamically optimal compression of the heart.

Further still, it is an object of the present invention to provide a device having provisions to accomplish cardiac defibrillation, while at the same time allowing for the detection of abnormal electrocardiograph rhythms, or if needed, provisions for stabilizing the heartbeats during cardiac arrest by electrical cardiac pacing.

SUMMARY OF THE INVENTION

The present invention is directed to a massager and a method both to be used to accomplish internal cardiopulmonary resuscitation (CPR). The massager is a manually operated cardiac compressor that is used to sustain the blood flow of the body during periods of cardiac arrest, and has various embodiments each of which allows for a minimal thoracic incision for the massager's safe, intrathoracic introduction and positioning.

The direct, intrathoracic heart massager comprises a heart-contacting member having a surface which is at least partially concave for contacting the heart, a handle means attached to the heart-contacting member for manually manipulating the massager, and, preferably, cushioning means on the surface of the contacting member.

The method for performing the heart massage comprises the following steps: providing a heart massager having a heart-contacting member connected to a handle and which member is at least partially concave for contacting the heart; making an incision into the skin at the intercostal space, preferably in the fourth intercostal space, between the left nipple and the lateral border of the sternum; surgically separating the intercostal space; inserting the heart massager through the intercostal space and onto the apex region of the heart; and then, periodically and manually pressing and releasing the handle so that the heart is alternately compressed and allowed to return to its non-compressed state.

Other objects, advantages and novel features of the present invention will become apparent in the following detailed description of the invention when considered in conjunction with the accompanying drawings.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 1 illustrates a heart massager in accordance with one embodiment of the present invention.

FIG. 2 is a view, taken along line 2—2 of FIG. 1, showing further details of the embodiment of FIG. 1.

FIG. 3 is a partly-broken-away view of a heart massager having shock absorber means so as to prevent any possible damage to the heart due to excessive compression force during its massage.

FIG. 4 illustrates a heart massager having pressure release means so as to prevent any possible damage to the heart during its massage.

FIG. 5 is a view, taken along line 5—5 of FIG. 4, partly broken away to illustrate further details of the embodiment of FIG. 4.

FIG. 6 illustrates another embodiment of the present invention having a plunger-like shape with an inflatable/deflatable sidewall.

FIG. 7 is a view, taken along line 7—7 of FIG. 6, illustrating further details of the inflatable/deflatable cup massager of FIG. 6.

FIG. 8 illustrates another embodiment of the present invention having suction-cup members that assist in having the ventricular chambers of the heart move outward so as to reseek their non-compressed condition; thereby, enhancing the filling (diastole) cycle of the heart during its massage.

FIG. 9 illustrates an umbrella arrangement for a radially expandable/compressible cup member that allows for the placement of the massager onto the heart by way of an incision of less than about one inch long in the intercostal space between the ribs of the body.

FIG. 10 is a view, taken along line 10—10 of FIG. 9, showing further details of the telescopic arrangement of the handle and cup members comprising the umbrella massager of FIG. 9.

FIG. 11 partially illustrates the compressed condition of the cup member of FIGS. 10 and 11.

FIG. 12 illustrates an expandable heart massager inserted through an optical endoscope. Wiring for an electrocardiograph, cardiac pacing device, and defibrillator pass through the handle of massager to electrodes in the heart-contacting member.

FIG. 16 is a view illustrating the placement of the massager onto the heart.

FIG. 17 is composed of FIGS. 17A and 17B which respectively illustrate the heart in a non-compressed condition and the compression of the heart in the anterior-posterior direction.

FIG. 18 is composed of FIGS. 18A, 18B and 18C which respectively illustrate the heart in a non-compressed condition, the compression of the heart in the lateral-medial direction, and the partial occlusion of the aorta.

DESCRIPTION OF THE PREFERRED EMBODIMENT

Figure 13:
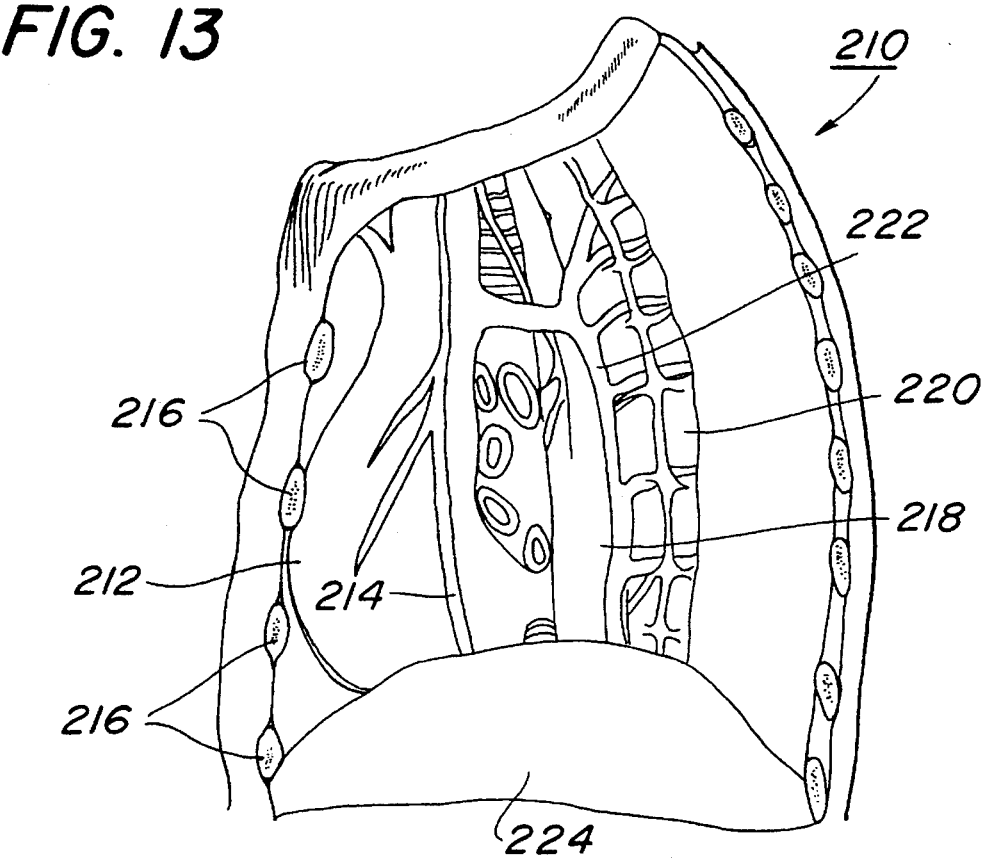
FIG. 13 illustrates a right lateral view of the thorax showing, among other things, the location of the heart.

Referring to the drawings comprising FIGS. 1–18, wherein like numerals indicate like elements, there are shown in FIGS. 1–12 various embodiments of the heart massager of the present invention, whereas FIGS. 13–18 show the anatomical elements of the body related to the method of the present invention.

The instant invention is related to massagers and a particular method for their usage that allows each massager to be inserted through a small surgical opening made in the chest wall, so as to allow the massager to directly contact the anterior antero-lateral surface of the human heart. Each of the massagers of the present invention is manually operated to accomplish a direct substernal massage of the heart so as to induce alternate cycles of compression and relaxation; thereby, sustaining blood circulation to facilitate resuscitation of the heart from its cardiac arrest condition. Manual compression and relaxation of the massager produce pulsatile blood-flow patterns similar to the normal ventricular filling and contraction of a healthy heart. In various embodiments, features are provided that allow for direct internal cardiac defibrillation, detection of abnormal electrocardiac rhythms, cardiac pacing and/or relocation of the massager during the heart massage, to optimize results obtained through manual compression of the massager.

The massager has various embodiments, all with padded-concave members having features particularly suited to accommodate different aspects of the heart massage. In one embodiment, an umbrella arrangement is provided which holds a padded cup member in its collapsed condition until the device is subcutaneously introduced through a surgical incision in the intercostal space, and, then, allows for the radial expansion of the sidewall of the cup member so that it directly contacts the heart. In other embodiments, various means are provided to prevent the massager from being pressed downward with excessive force or to rapidly, each of which might otherwise damage or scar the heart being massaged. Still further embodiments are provided that have concave members to contact the heart in a conformal manner so that the following features are provided: (1) a gripping action of the surface of the heart during the massage; and (2) a sucking effect on the surface of the heart so as to allow the heart to expand outward as the massager is moved or lifted upward; thereby, enhancing the filling cycle of the chambers of the heart.

In its operation, and in a general manner, the massager is inserted into the left chest via a small surgical incision. The massager has a heart-contacting member that is subcutaneously inserted through the incision and into the interior of the chest so that the now substernal massager may be placed on the anterior and lateral surfaces of the ventricular chambers of the heart. The massager allows the operator to manually compress the heart, which is confined by the pericardium, against the posterior chest wall structures. This manual compression results in an ejection of blood from the ventricular chambers similar to that occurring during normal cardiac contraction (systole). The massager is then relaxed so that the heart is allowed to fill passively (diastole). All of the embodiments of the present invention advantageously allow the heart to be compressed manually without the requirement of any external device, such as a pneumatic apparatus.

As described herein, the massagers of the present invention have heart-contacting member having different forms but all forms of the heart-contacting members have a shape so that surface of the member contacting the heart is concave. This concaveness advantageously serves to conform the shape of the contacting surface of the massagers to the surface of the heart. Each of the heart-contacting members has no dimension that is greater than three inches.

As further described herein, the massagers of the present invention are subjected to a downward-axial force that most commonly occurs because the patient, who is receiving the heart massage, is commonly in the lying-down position. The massagers of the present invention may be subjected to forces in any direction necessary so as to accommodate any of the possible positions of the patient receiving the heart massage.

Still further, as described herein, some of the massagers of the present invention have a telescopic arrangement, wherein tube members move in an axial direction relative to each other or move in an axial direction in unison.

As shown herein, the concavity of the heart-contacting member may take the shape of a cup. The cup member has the appearance of a plunger except that its portion of the plunger contacting the heart is closed. The cup has one end which is open and receives a handle and another end which is closed by a diaphragm having a concave shape for contacting the heart and a predetermined diameter. The ends are joined by a flexible sidewall which flares outward from the handle.

One of the embodiments of the heart massager may be further described with reference to FIG. 1. The figure illustrates a massager 10 preferably having a grip 12, and comprised of a handle 14, a heart-contacting member 16 and, preferably, cushioning means 18 and padding means 20. The heart-contacting member 16 is attached to one end of the handle 14 and has a surface 16A, shown in FIG. 2, which is at least partially concave for contacting the heart. The heart-contacting member, in the form shown in FIGS. 1 and 2, is a concave plate and has edges 16B and 16C.

The embodiment 10 has some of the features of the well-known "Richardson Retractor" commonly used to hold back or retract elements of the abdominal wall to facilitate exposure of this wall during abdominal operations. The retraction of the abdominal wall is achieved by pulling on the handle of the Richardson retractor which has a handle similar to the present invention. However, the bottom portion of the Richardson retractor has a hoe-like retracting blade, whereas the present invention has a smoothly, contoured concave plate 16 having means to allow it to conform to the surface of the heart during its usage, and does not have any of the blade-like features of the Richardson retractor. Furthermore, the Richardson retractor is used as a pulling device, whereas the present invention is used as a pushing device for pushing against the heart. Further details of the massager 10 may be described with reference to FIG. 2, which is a view taken along line 2—2 of FIG. 1.

The cushioning means 18 provides a cushioning action for the heart as the handle 14 is typically pressed downward. The cushioning means 18 is contoured so as to match the shape of the heart which the massager contacts. The cushioning means 18, in cooperation with the concave plate 16, provides a massager that conforms to the surface of the heart being massaged. The handle 14 and the heart-contacting member 16 are both preferably of a plastic material to facilitate electrodes and wiring therefor, along with other electrical functions (e.g., defibrillation, cardiac pacing and EKG).

The cushioning means 18 comprises deformable material having a portion 18A that conforms to the shape of the surface 16A of the concave heart-contacting member 16, and a portion 18B which generally conforms to the shape of the anterior surface of the heart. The heart-contacting member 16 has edges 16B and 16C which are spaced apart from each other by a distance 16D in a manner corresponding to a typical concave shape, such as that of heart-contacting member 16 shown in FIG. 2. The portion 18B and, preferably, at least the edges 16B and 16C of the heart-contacting member 16 are covered with a padded material 20, preferably a foam rubber or plastic in which two electrodes are embedded and have wiring routed through handle 14. If desired, this material 20 may be formed as a part of cushioning means 18. The pad 20 has an uneven, non-smooth surface that provides a slight gripping action which assists the external mating surface of the massager 10 to remain in contact, during the heart massage, with only one region of the heart. This assistance is desired so that once the massager is placed onto the desired location (to be described) of the heart, it remains at this location even in spite of the upward-downward movements of the handle 14 normally occurring during the massage of the heart.

The embodiment 10 of FIG. 2 as well those massagers of the FIGS. 3–8 have an overall dimension such as that defined by 16D, shown in FIG. 2, that is measured from the tip of each of the edges 16B and 16C, and is of a value of less than about three (3) inches. As will be described, this three inch dimension is also pertinent to the diameter of the heart-contacting members having a cup shape, shown in FIGS. 3–8. As will be further discussed with regard to the embodiment of FIGS. 9–11, this three inch dimension may be further reduced to be less than about one inch.

Another embodiment 22 of a substernal heart massager, having shock absorbing or damping means for absorbing energy of sudden impulses that might accidently be applied to the massager 22 and might otherwise damage or scar the heart being massaged, is disclosed in FIG. 3. The massager 22 of FIG. 3, as well as the massagers of FIGS. 4 and 5, comprises the heart-contacting member 16, cushioning member 18 and pad 20 all of which have already described with reference to FIG. 2. The apparatus 22 of FIG. 3 also includes various elements having reference numbers all of which are given in the below Table 1.

TABLE 1

Apparatus 22

| Reference No. | Element |
|---|---|
| 24 | first telescopic tube |
| 26 | second telescopic tube |
| 28 | guide slot formed in tube 24 |
| 30 | adjustment screw located in slot 28 and affixed to tube 26 |
| 32 | compressible material comprising the shock absorbing means of massager 22 |
| 34 | electrode for transmitting electrical pulses or receiving electrocardiographic impulse |
| 36 | electrode for transmitting electrical pulses or receiving electrocardiographic impulses |
| 38 | opening in foot member 16 |
| 40 | conductor connected to electrode 34 |
| 42 | conductor connected to electrode 36 |
| 44 | gourmet abutting between conductor 34 and opening 38 |
| 46 | gourmet abutting between conductor 36 and opening 38 |
| 48 | plug for accepting signals from a cardiac stimulator for defibrillation/cardiac pacing |

The upper telescopic tube 24 has one of its ends connected to grip 12 and its other end movable within one end of the tube 26 which, in turn, has its other end connected to the heart-contacting member 16. The tube 24 has a predetermined diameter that allows for movement in an axial direction relative to tube 26. The guide slot and adjusting screw 30 provide the means for limiting the distance of relative motion (axial movement), in both the upward and downward directions, between the tube 24 and tube 26. More particularly, the positioning or tightening of the screw 30 within the slot 28 of tubular member 24 allows for axial movement of tube 24 relative to tube 26, until screw 30 engages the upper end of guide slot 28. The amount of relative movement is determined by the axial-lengthwise dimension of guide slot 28. During the downward movement, the compressible material 32 acts as a shock absorber to absorb the energy of any sudden downward-axially forces that may be imparted to tubes 24 and 26. This shock absorbing means 32, preferably of a spongy material, absorbs this unwanted sudden force that might scar, irritate or otherwise damage the heart organ. The spongy material 32 absorbs or dampens the accidental forces that might otherwise be imparted to the heart organ.

The massager 22 further comprises electrodes 34 and 36 that extend out of and exposed by padded member 20. The electrodes 34 and 36 are routed to a cardiac stimulator (not shown), commonly referred to as defibrillator, by means of conductors 40 and 42, respectively, that pass through the handle and out the top of grip 12. The cardiac simulator may also have provisions for cardiac pacing to be described hereinafter. Gourmets 44 and 46 respectively separate conductors 38 and 40 from the heart-contacting member 16.

In operation, the defibrillator (not shown) supplies electrical pulses, by way of an external conductor (not shown) and plug 48, to the electrodes 34 and 36 which are in contact with the heart tissue, so as to terminate the ventricular fibrillation which most commonly causes cessation of spontaneous cardiac pumping action. Alternately, the electrodes 34 and 36 may be arranged to serve as sensors for receiving electrocardiographic impulses and converting such impulses into appropriate electrical signals for transmittal to cardiac pacing equipment.

Another embodiment shown in FIG. 4 as massager 52 has means for releasably engaging tubes forming a telescopic handle allowing for unison movement of the tubes in their engaged condition. The releasably engaging means further comprises resilient biasing means for releasing the engagement of tubes when the force applied to the tubes exceeds a predetermined limit. An indicator is also preferably provided to notify the operator that this force limit has been exceeded. The massager 52 has an actuator assembly 54 in the form of a telescopic arrangement. The telescopic assembly 54 a first tube 56 having one end connected to the grip 12 and its other end having dimensions selected to allow movement, in an axial direction, relative to a second tube 58 which, in turn, has its other end connected to the heart-contacting member 16. Further details of the massager 52 may be described with reference to FIG. 5, which is a view taken along line 5—5 of FIG. 4.

FIG. 5 shows an assembly 60 that serves as the means for releasing engaging the first and second tubes 54 and 56, respectively, and also provides the resilient biasing means for releasing the engagement of the tubes when the force applied to the tubes exceeds a predetermined limit. The forces are applied, usually in a vertical-downward direction, to the grip and, thus to the handle comprised of both telescopic tubes. It is preferred, that an indicator be provided to warn the operator when the limit has been exceeded. The assembly 60 is comprised of elements having reference numbers all of which are given in the below Table 2.

TABLE 2

Assembly 60

| Reference No. | Element |
|---|---|
| 62 | groove in sleeve 58 |

TABLE 2-continued

Assembly 60

| Reference No. | Element |
| --- | --- |
| 64 | ball |
| 66 | spring means |
| 68 | screw means |
| 70 | contact switch |
| 72 | excessive pressure warning indicator |

In operation, screw 68 is adjusted so as to establish the degree of force that pushes the ball 64 against the wall of groove 62. The ball-groove contact provides the engagement between the tubes for the engagement between the tubes 56 and 58 allowing them to move in unison in an axial direction. This spring adjustment also determines the amount of force needed to cause the ball 64 to move out of the groove 62 which, in turn, allows the tube 56 to surge downward in a vertical direction relative to tube 58. The operator, upon sensing such a surge, responds by removing or relieving the downward force applied to the massager 52 by way of grip 12, thereby, avoiding any possible damage to the heart through excessive application of force. Rather than rely on the operator's perception of the movement of tube 56 relative to tube 58, it is preferred to have the movement of ball 64 out of the groove 62 activate a switch 70 located below the groove 62 which, in turn, activates an excessive pressure warning indicator 72. This warning mechanism may also be provided by having a switch 70A, the same as switch 70, located on tube 56 and above tube 58. The switch 70A only comes into contact with tube 58 when the ball 64 moves out of the groove 62. The alternate arrangement of switch 70A allows tube 56 and tube 58, both of actuator assembly 54, to be more easily separated during the adjustment procedure of the spring 66-screw 68 arrangement.

A further massager 74 of the present invention, having inflatable/deflatable characteristics and the appearance of a plunger device, is shown in FIG. 6. The massager 74 has a handle 76 in the form of a tube with the grip 12 affixed to its upper end, first conduit means 78 which communicates with a source of positive fluid (liquid or gas) pressure and is affixed to handle 76, second conduit means 80 connected to a source of negative fluid (fluid or gas) pressure and affixed to the handle 76, and a heart-contacting member 82 having a flexible sidewall 84 and one end 86 that generally conforms to the surface of the heart. Each of the conduit means 78 and 80 is in the form of a flexible tubular member.

The heart-contacting member 82 comprises a cup having one end which is open and receives the handle 76 and another end which is closed by a diaphragm 86 having a concave shape for contacting the heart and a predetermined diameter. The ends of the cup 84 are joined by the flexible sidewall 84 which flares outward from said handle 76.

The source of positive fluid pressure used for the massager 74 may be in the form of a cartridge preferably containing $CO_2$ or liquid water both under pressure, but may alternatively contain pressurized air. The source of negative fluid pressure used for the massager 74 may be a syringe or some other suction-generating source. The massager 74 may be further described with reference to FIG. 7, which is a view taken along line 7—7 of FIG. 6.

The handle 76 has an opening 76A at one end that allows for the ingress, shown by arrow 88, and egress, shown by arrow 90, of fluid entering into and exiting out (respectively) of the cup member 82. The ingress and egress of such fluid is controlled by fluid control means 92 comprising an assembly of elements having reference numbers all shown in the below Table 3.

TABLE 3

Control Assembly 92

| Reference No. | Element |
| --- | --- |
| 94 | control knob |
| 96 | needle member |
| 98 | guide means for needle member 96 |
| 100 | L-shaped conduit |
| 102 | sealing member |

In operation, the control means 92 either lets a fluid medium, such as the medium $CO_2$, air raised to a positive pressure or liquid water under pressure, into the cup member 82, or allows for the escape of this medium from the cup member 82 back to the source of positive liquid pressure. The manual control of this ingress or egress of the fluid medium is accomplished by means of the knob 94 opening or closing a valve (not shown) in L-shaped conduit 100. The knob 94 may be arranged so that its depression causes the inward movement of needle 96 which, in turn, engages a valve seated in an opposing wall of the L-shaped conduit 100, so as to allow the medium under positive pressure, shown by arrow 88 entering into the first conduit means 78, to pass through the L-shaped conduit 100 near the top of the handle 76 and into the cup 82, thereby, causing the laterally flexible wall 84 of cup 82 to expand outward and into its operative state ready to be used in the performance of the heart massage. In such an expanded state, the sealing member 102, preferably of a silicone material in its hardened state, prevents the medium raised to a positive pressure in the cup 82, from passing upward from control means 92. Sealing member 104, preferably of a silicone material, prevents the medium, raised to the positive pressure, within cup 82 from finding its way out through the upper portion 84A of the flexible cup sidewall 84.

When it is desired that the cup member 82 be placed into its non-operable state, for insertion or removal from chest, the source of positive fluid pressure is removed from the first conduit means 78, and the knob 94 is depressed causing the needle member 96 to move outward and thereby open the valve in member 100. This allows the medium ($CO_2$, liquid water or air raised to a positive pressure) trapped in the cup 82 to find its way out of the cup 82 by way of the L-shaped member 100, in the direction as shown by arrow 90.

Negative fluid pressure acting as a suction source, may be is applied to the cup 82 by way the second conduit means 80 that has a tube or channel running into the open end 76A of handle 76. The second conduit means 80 may further comprise control means (not shown) for selectively activating and deactivating the negative pressure entering handle 76, but such a pressure-selective control device may also be arranged in the negative fluid pressure source itself. The suction effect provided by means 80, causes the concave-conforming surface of diaphragm 86 of the cup 82 to more effectively grip onto the heart allowing for enhanced pumping of blood through the heart during the CPR method of the present invention to be described hereinafter.

A further massager embodiment 106, partially shown in FIG. 8, is designed to also assist in the filling process (diastole) of the heart that occurs during the heart massage. Massager 106 has a handle 108 having within its hollow a suction channel 110 similar to the suction channel of device 80 of FIG. 7. The handle 108 of FIG. 8, has a heart-contacting member 112 in the shape of a cup connected to its open end 108A and sealed thereto by sealing means 114 preferably of a silicone material. The heart-contacting member 112 serves the same function as the heart-contacting member 16 having the form of a concave plate of FIG. 1 and has a cup-like shape and a structure very similar to the cup-like heart-contacting member 82 of FIGS. 6 and 7. The heart-contacting member 112 has a continuous sidewall 116, and one end 118 with a predetermined diameter and its other end connected to said opened end 108A of the tubular handle 108. The sidewall 116 expands outward when subjected to an applied downward force. The end 118 has an outer surface with a plurality of circular shaped indentations 120 comprising suction-cups members. The outer surface has this concave shape so as to be adapted for contacting the heart.

In operation, the suction cups 120, in cooperating with the suction channel 110 connected (not shown) to a source of negative fluid pressure, provide a sucking or gripping effect for the massager 106 onto the surface of the pericardium, so that the muscle of the heart along with its blood controlling chambers are expanded outward upon the upward movement of the handle 108 of the massager 106. This upward movement of handle 108 expands the heart muscle so as to enhance the filling of its heart chambers during the relaxation period of the CPR process to be described.

Another embodiment of the present invention, having umbrella-like features and allowing for its insertion through the chest by way of a surgical incision of less than about one inch, is shown in FIG. 9 as massager 122. The umbrella-like massager 122 has a handle 124, in the form of a telescopic arrangement, and a concave cup member 126 which is compressible and radially expandable in response to a force applied to its outer surface.

In general, the handle 124 comprises first and second telescoping tubes for axial movement relative to each other, one of the tubes being connected to the grip 12. The first and second tubes are interconnected by a rod with a carriage member on an end thereof and displaceable within the tubes. The carriage member has affixed thereto a plurality of flexible spoke members. The flexible spoke members each having one end affixed and circumferentially spaced apart from each other in the carriage member. Each of the flexible spoke members further has its other end axially extending out of the carriage member. The collapsible cup comprises stretchable material and has flexible sidewall having means for respectively capturing and holding each of the other ends of the flexible spoke members axially extending out of the carriage member.

More particularly, the collapsible cup 126 has a plurality of flexible ribs 128, a plurality of flexible body portions 130, and, preferably, a cushion member 132 that extends around the lower rim portion of cup 126 as seen in FIG. 9. The massager 122 further comprises sensors/electrodes 134 and 136 located on the circumference of the cushion member 132 and which are respectively routed to plug 138 via conductors 140 and 142 for connection to a defibrillator or cardiac simulator. The operation of the sensors/electrodes will be described below, in connection with the description of FIG. 12. The massager 122 preferably has third conduit means in the form of a flexible tubular member that extends into a hollow of the handle 124 and which is connected (not shown) to a source of negative fluid pressure to provide the suction effect of the heart muscle in a manner as described with reference to conduit means 80 and 110 of FIGS. 7 and 8 respectively. The massager 122 may be further described with reference to FIG. 10, which is a view taken along line 10—10 of FIG. 9.

FIG. 10, in addition to those elements shown in FIG. 9, illustrates a plurality of elements given in the below Table 4 along with their respective reference number

TABLE 4

Massager 122

| Reference No. | Elements |
| --- | --- |
| 146 | first tube member of telescopic handle 124 |
| 148 | second tube member of telescopic handle 124 |
| 150 | central pole interconnecting tubes 146 and 148 |
| 152 | attaching means for pole 150 |
| 154 | carriage member for riding and being displaced within tube 146 |
| 156 | plurality of flexible spoke members |
| 158 | outer surface of a piece of stretchable material having a cup-like shape in its expanded state |
| 160 | inner surface of the stretchable flexible material having a cup-like shape in its expanded state |
| 162 | bottom concave surface of the cup-like flexible material |

The tube 146 has a bore with a predetermined dimensions, and an exit portion. As best illustrated in the upper portion of FIG. 10, the tube 148 has a predetermined outer dimension selected to allow the tube 148 to move within the bore of the tube 146 in a reciprocating manner. The tube 148 is connected (not shown) to the grip 12.

The central pole 150 has one end affixed to the inner diameter of the tube 148 by attachment means 152 and has its other end glided within the bore of the tube 146 by carriage member 154. The carriage member 154 rides and is displaced within the tube 146. The attachment means 152 may be of any suitable form such as welding so long as the pole 150 remains fixed to the tube 148 during the reciprocating movement of tube 148. The carriage member 154 has affixed therein a plurality of flexible spokes 156, each being circumferentially spaced apart from each other and each vertically extending downward from the carriage member 154.

The compressible and radially expandable cup member 126 comprises a stretchable material and is connected to the carriage member 154 by means of the plurality of spoke members 156 that are lodged and held in each of the ribs 128 of the expandable material by appropriate capturing means affixed to the expandable material. As best seen in the lower portion of FIG. 10, the ribs 128 are bowed outward by the action of their captured radially-expanding spokes 156.

In operation, the massager 122 operates in a similar manner as a conventional umbrella allowing the stretchable material to have a cup-like shape in its expanded condition and a tubular-like shape in its compressed condition. When grip 12 is retracted upward relative to tube 146, the carriage member 154 moves upward, as viewed from FIG. 10, which correspondingly causes the spoke members 156 to be withdrawn upward which, in turn, results in the ribs 128 being pulled radially inward until all the cup-like shaped material is compressed and drawn into the tube 146. Such a compressed condition is shown in FIG. 11, wherein it is seen that spoke members 156, in their relaxed condition, merge at a central region 164 and taper outward therefrom toward both their upper and lower regions. This compressed condition is used for the insertion and withdrawal of the massager 122 from the chest cavity. With further reference to FIG. 11, the maximum outer diameter of the cushion member 132, shown as dimension line 132A, is preferably less than about one inch. Such a dimension allows the umbrella massager to be first inserted into a surgical incision of less than one inch for later intra-thoracic positioning of the massager to accomplish the massage of the heart muscle.

The cup member 126 is closed off by the bottom wall 162 which has a flexible diaphragm-like concave shape to adapt to the surface of the heart. When it is desired to cause the cup member 126 of FIGS. 9–11 to radially expand outward from its compressed condition so as to obtain its operative state, the grip 12 is gripped by the operator and a force is applied so that the grip moves toward the exit portion of tube 146. As viewed from FIG. 10, this movement in turn causes the carriage member 154 to move downward which, in turn, causes or allows the spoke members 156 to move the ribs radially outward until all of the cup-like shaped material of cup 126 is expanded outside of the tube 146. Following its use, the umbrella massager 122 is retracted into its tube 146 for removal from the chest cavity.

A still further embodiment, massager 166, of the present invention is shown in FIG. 12 having provisions for receiving signals transmitted from a plurality of external devices. The massager 166 has a handle 168 to which is mated, at a slight angle, a collar 170 of an endoscope 172 that accepts a cable 174 routed from an endoscopic light source 176. The endoscope 172 has a cable 178 that runs downward into the lower portion of handle 168 to direct the related light thereto and is used by the operator of endoscope for viewing purposes. The endoscope may be any of the known commercially available endoscopes.

The massager 166 has sensors/electrodes 134 and 136 in the heart-contacting member 126 having a cup like shape and that contacts the heart during massage. In one form, that is, the sensors 134 and 136 act as elements for receiving signals such as impulses generated by the heart, whereas in another form that is, electrodes transmit electrical pulses received from a defibrillator. The sensors/electrodes are connected by internal cabling (not shown) that exits handle 12 as cabling 184 which, in turn, is connected to a switching device 186. The device 186 selectively interconnects the massager 166 to one or more of the external devices given as follows: (1) electrocardiograph 188; (2) cardiac pacing device 190; (3) defibrillator 192; and (4) excessive compression pressure warning light 72. Each of the electrocardiograph 188, the cardiac pacing device 190 and the defibrillator 192 may be of a known commercially available type. The mechanism that controls the warning light 72 is not shown in FIG. 12, but is shown and has been described with reference to FIG. 5. The devices 188, 190, 192 and 72 assist or enhance the operation of the massage of the heart and are respectively interconnected to switch 186 by means of cables 194, 196, 198 and 200.

In operation, the endoscopic device 172 allows the massager 166 to be guided in a very accurate manner to its desired position of the heart. The device 172 allows the operator to see the subcutaneous movement of the concave-cup 126, serving as the foot of the massager 166, so that the foot may be exactly placed onto its desired location on the heart during the heart massage.

The selection of device 188 by switch 186 allows the electrocardiogram (EKG) to record the changes in the electrical potential caused by the heartbeat. Such changes may be used to determine and correct for any abnormal electrocardiograph rhythms that may be present during the CPR procedure involved in the cardiac arrest.

The selection of device 190 by switch 186 may be used to synchronize and stabilize the EKG signals created by the heartbeats during the cardiac arrest condition. The stabilization provided by device 190 may assist in a more rapid recovery from a cardiac arrest condition.

The selection of device 192 by switch 186 may be used, as previously discussed, for defibrillation of the heart muscle to allow it to return to its normal operating condition in a more rapid manner.

Another instrument (not shown) that finds particular usage with the practice of the present invention and that is external from the massager 166, is a blood pressure monitor unit that normally contacts the patient by means of a cuff device. This monitor is used to detect the increased flow of blood generated by the CPR techniques of the present invention relative to the closed CPR techniques of the prior art. This elevated blood pressure may be used as a tool or indicator that a hemodynamically significant compression of the heart organ is actually taking place during the internal CPR, to be described, using the present invention. The blood pressure may be used a monitoring means to advantageously place, maintain or move the massagers of the present invention to or from desired positions along the heart, so that the compression thereof causes the advantageous enhancement of the blood flow as manifested by elevated blood pressure during the internal CPR procedure.

It should now be appreciated that the practice of the present invention provides for various massagers all having special provisions for allowing for increased blood flow, while at the same time being of relatively small dimensions to minimize the surgical incision necessary for the internal CPR technique of the present invention.

Figure 14:
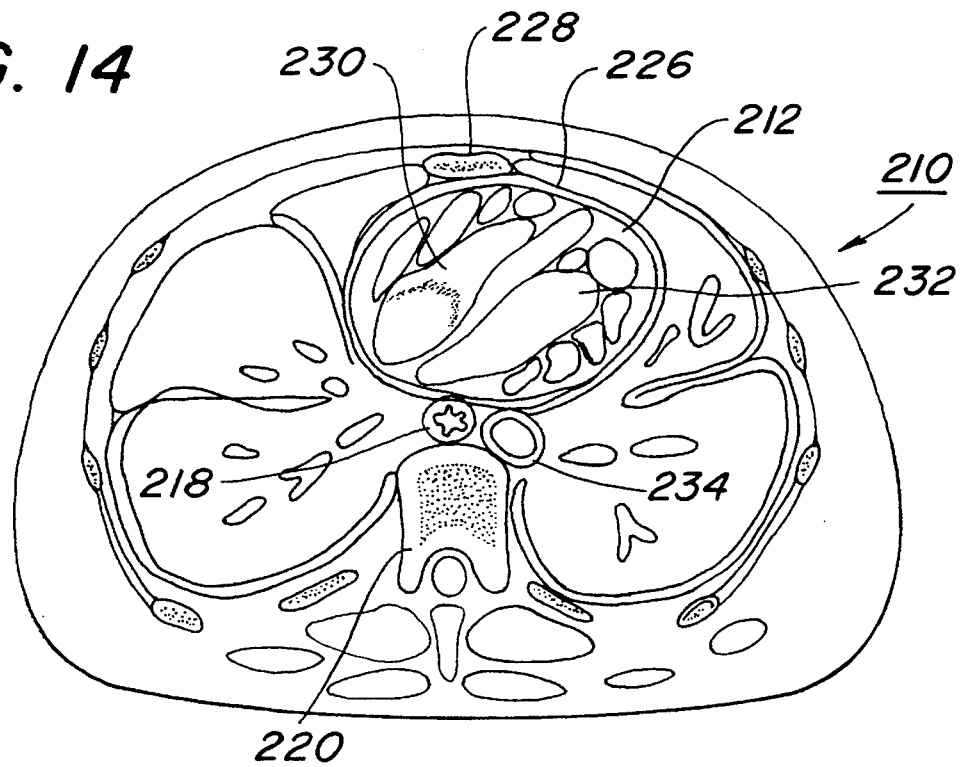
FIG. 14 is a cross-sectional view of the thorax of FIG. 13.
Figure 15:
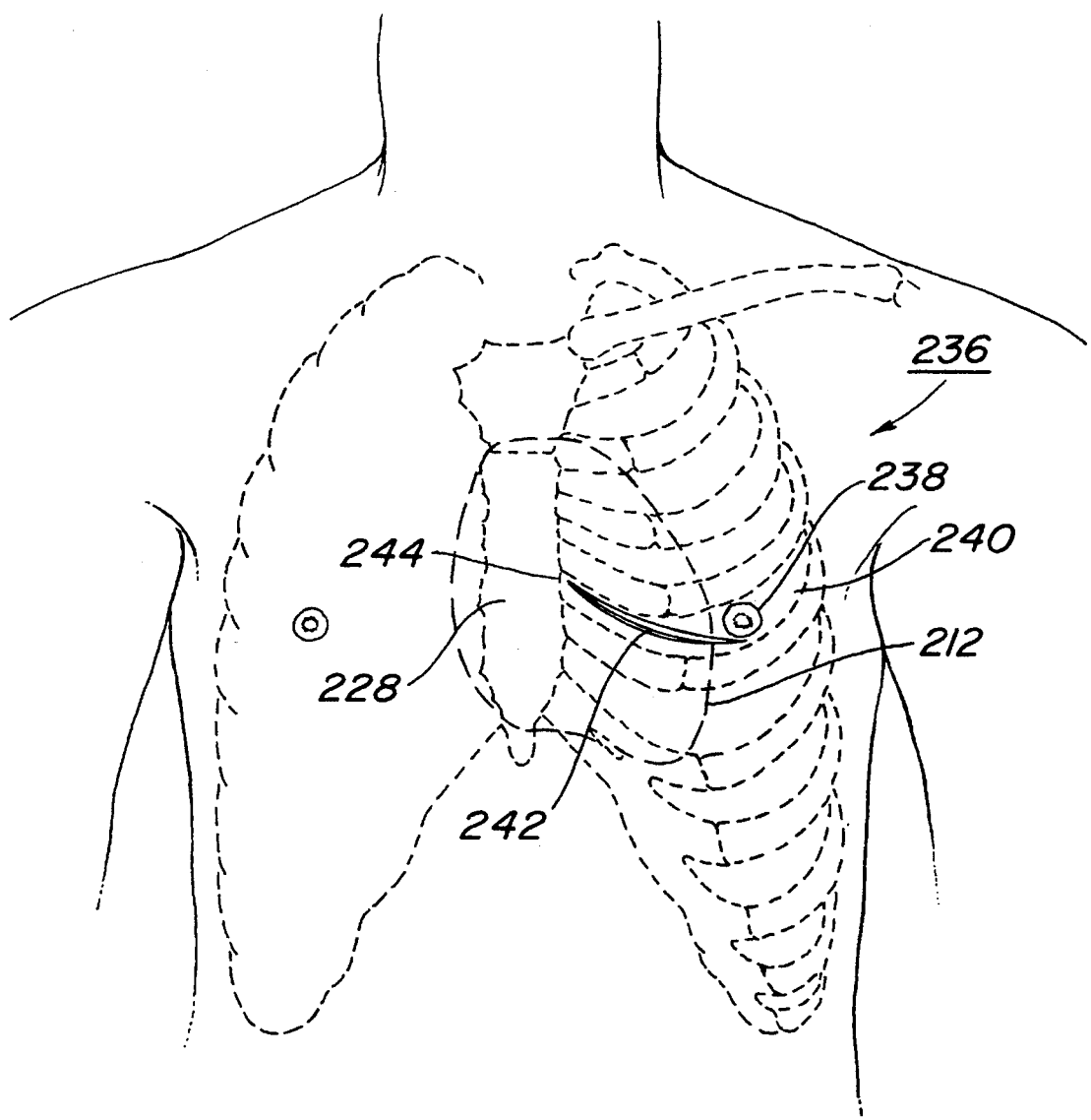
FIG. 15 is a view showing the location of the surgical incision for introducing the massagers onto the heart.

Method and Technique for Internal
Cardio-Pulmonary Resuscitation (CPR) of the
Present Invention The method of the present invention may be described with reference to FIGS. 13–18 in which FIGS. 13 and 14 illustrate the location of the anatomical elements related to the present invention; FIGS. 15 and 16 illustrate the predetermined location of surgical incision of the present invention; FIG. 17, composed of FIGS. 17A and 17B, illustrates the anterior-posterior compression of the heart achieved according to the practice of the present invention; and FIG. 18, composed of FIGS. 18A, 18B and 18C, illustrates the lateral-medial compression of the heart achieved according to the practice of the present invention.

FIG. 13 is a right lateral view of the thorax (chest) 210 showing the human heart 212 located in its lower portion. FIG. 13 further illustrates the location, relative to the heart 212, of the phrenic nerve 214, the ribs 216 (the plurality of ribs being indicated by a single reference number 216), the esophagus 218, vertebrae 220, azygous vein 222 and diaphragm 224. Further details of the heart 212 are shown in FIG. 14 which is a cross-sectional view of the thorax.

The heart 212 is enclosed in a tough, fibrous sac called the pericardium 226, which is attached by fibrous strands to the posterior portion of the sternum 228. The heart 212 has right and left cardiac ventricles 230 and 232, respectively, which propel blood into the heart and the body, commonly called systemic circulation. As shown in FIG. 14, behind the heart 212, overlying the thoracic vertebrae 220, are located the esophagus 218 and the descending aorta 234 (the main artery carrying blood to the body from the heart). The particular arrangement of these anatomical features lend themselves to the ability of the massagers of the present invention to provide the desired compression of the heart in both the anterior-posterior and the lateral-medial directions once these massagers are intra-thoracically and substernally positioned. The positioning of any of these massagers may be described with reference to FIG. 15 showing the rib cage 236 of the body.

FIG. 15 primarily illustrates the left side of the rib cage 236, as well as the location of the heart 212 (shown in phantom) relative to the left nipple 238, sternum 228 (shown in phantom) and the fourth intercostal space 240. As shown in FIG. 15, a small surgical incision 242 is made in the fourth intercostal space 240 between the fourth and fifth ribs, approximately 1–3 inches in length. This incision 242 is created on the anterior chest wall along a line between the left nipple 238 and the lateral border 244 of the sternum 228. This 1–3 inch incision is applicable for the use of the massages illustrated in FIGS. 1–8 and 12. The massagers of FIGS. 9–11 require only an about one (1) inch incision.

Unlike the known prior art methods such as that of the '932 patent discussed in the "Background" section above, the surgical incision 242 of the present invention does not enter the upper abdomen beneath the xiphoid process of the sternum, but is made in the left chest over the ventricles of the heart. After such an incision is made, a sharp surgical instrument is used to provide sharp dissection, preferably in the fourth intercostal space, thereby, allowing for the entrance of the finger of an operator which is used to locate, by finger palpation, the apex region of the heart. The massager, such as massager 10 of FIG. 1 having the heart-contacting member with a surface which is at least partially concave for contacting the heart 16, may now be introduced onto the heart and such introduction may be described with reference to FIG. 16.

FIG. 16 shows the massager 10 introduced through the ribs which are shown as $216_2$, $216_3$, $216_4$, $216_5$ and $216_6$ with the subscript indicative of the particular rib of the body. The massager is inserted between the fourth $216_4$ and fifth $216_5$ ribs and onto the apex region 246 of the heart 212.

The incision provides for the entrance of any of the massagers of the present invention between the ribs and allows such massager to be placed on the heart muscle without incising the pericardium. Cardiac compression is then carried out by manual depression of the introduced massager. The compression of the heart may be described with reference to FIGS. 17 and 18.

FIG. 17A shows the right and left ventricles 230 and 232 as being divided by septum 248. FIG. 17A further shows heart 212 in its non-compressed state, whereas FIG. 17B shows heart 212 in its compressed state created by a pressure applied to the massager 10. The compression is predominantly in the anterior-posterior direction 250, thereby compressing, as shown in FIG. 17B, both the right and left ventricles 230 and 232. However, the manual stroke also has a lateral-medial component, which is described with reference to FIG. 18.

FIG. 18 is composed of FIGS. 18A, 18B and 18C which respectively illustrate the esophagus 218 and aorta 234 located between the vertebrae 220 and the heart 212 shown in its non-compressed condition, an initial compressed condition of the heart 212, and a final compressed condition of the heart 212.

As seen in FIG. 18A, the esophagus 208 and aorta 234 are in their non-restricted state when the heart 212 is in its non-compressed condition.

FIG. 18B illustrates the initial contact of massager 10 with the heart 212. The massager 10 is shown in FIG. 18B in an enlarged manner, relative to that of FIGS. 16 and 17B, so as to more clearly illustrate the conformity of the heart-contacting member of the massager 10 to the surface of the heart. As seen in FIG. 18B, when the massager 10 is pressed downward, a lateral-medial component 252 is applied to the heart causing the heart to compress the ventricles 230 and 232 against the vertebrae 220. The final compressed state of ventricles 230 and 232 is shown in FIG. 18C.

FIG. 18C shows the heart with the massager removed so as to more clearly illustrate the compressed state of the ventricles 230 and 232, as well as the compressed state of the esophagus and, more particularly, the compressed or restricted state of the aorta 234. Because of the anatomic location of the aorta 234, the compression stroke along the lateral-medial direction 256 also produces a partial occlusion of the aorta 234 which, in turn, as previously discussed, elevates the blood pressure to a greater degree in the upper portion of the body than in the lower part. This compression, as previously mentioned, selectively increases the blood flow of the heart and the brain. This selective increase in blood pressure and flow does not occur in conventional open-chest or closed-chest manual CPR techniques. Further, this increased blood flow, which is a significant advantage of the present invention, has never been reported during the prior art open-chest or closed chest manual CPR techniques.

In the practice of the present invention, since the pericardium is left intact, (unlike open bi-manual CPR) the pericardial sac holds the heart in a favorable position during compression and prevents dilation of the heart chambers. These factors may also improve resuscitation using the present invention.

It should now be appreciated that the method of the present invention provides an internal, manual CPR technique that increases the blood flow in the vital organs improving the probability of patient survival.

Results Achieved by the Heart Massager and Method Both of the Present Invention

A massager of the present invention was introduced using minimum invasive surgery directly onto the heart of ten separate swines for the performance of direct CPR in a manner as previously described hereinbefore. The results of the direct CPR massage of the ten swines of the present invention, herein termed minimally-invasive (MID) CPR, were compared against the results obtained from massaging the hearts of the ten swines using open chest (OC) CPR. The parameters monitored during both the MID CPR and OC-CPR massagers are given in the below Table 5.

TABLE 5

| Parameter | Units of Measurements |
| --- | --- |
| cardiac index (CI) | cc/kg/min |
| arterial (pH) | acidity/alkalinity on a scale from 0 to 14 |
| arterial lactate (AL) | mml/dl |
| mixed venous pO2 (pVO2) | mmHg |

For each swine, ventricular fibrillation was induced and the parameters of Table 5 were recorded every ten minutes (m) in which five minutes of recording was allocated to the OC-CPR massage and the remaining five minutes of recording allocated to the MID CPR. The initial (0 minutes) recording was assigned as the baseline (Base) for each of massage techniques. The results of the testing are given in the below Table 6.

TABLE 6

| Time | CPR | CI | pH | AL | pVO2 |
|---|---|---|---|---|---|
| Base | OC | 78.4 ± 27.9 | 7.42 ± 0.06 | 1.44 ± 0.48 | 53.8 ± 11.1 |
|  | MID | 78.4 ± 11.8 | 7.42 ± 0.10 | 1.30 ± 0.35 | 53.4 ± 24.7 |
| 10 m | OC | 26.8 ± 4.5 | 7.34 ± 0.09 | 4.56 ± 0.43 | 23.4 ± 2.6 |
|  | MID | 40.5 ± 9.5 | 7.31 ± 0.10 | 3.60 ± 1.24 | 24.2 ± 6.8 |
| 20 m | OC | 35.1 ± 12.4 | 7.31 ± 0.04 | 5.14 ± 0.70 | 25.8 ± 4.5 |
|  | MID | 39.5 ± 11.9 | 7.30 ± 0.10 | 4.56 ± 1.62 | 22.5 ± 8.9 |
| 30 m | OC | 26.7 ± 10.5 | 7.23 ± 0.10 | 5.86 ± 0.62 | 24.8 ± 6.0 |
|  | MID | 43.9 ± 5.5 | 7.26 ± 0.10 | 5.04 ± 1.80 | 23.7 ± 9.0 |

The values CI, pH, AL and pVO2 are expressed in the mean values obtained (±) standard deviation from these mean values.

From Table 6 it can be seen that all of the parameters measured during the method of the present invention (MID) were comparable or better than those obtained from the open chest (OC) CPR method.

It should now be appreciated that the practice of the present invention provides for an apparatus and a method for a heart massager that yields results that are comparable and even better than that obtained from the open-chest CPR requiring major cardiac thoracotomy.

The present invention may be embodied in other specific forms without departing from the spirit or essential attributes thereof and, accordingly, reference should be made to the appended claims, rather than to the foregoing specification, as indicating the scope of the invention.

What we claim is:

1. A method of heart massage, the method comprising the steps of employing a heart massager having a heart-contacting member with a heart-contacting surface which is at least partially concave, said heart-contacting member being connected to a handle, the heart-contacting member having a plane tangential to the member's concave surface in a region the handle is attached to the heart-contacting member, the handle being substantially upright with respect to the plane;

(a) making an incision in the skin in an intercostal space;
  (b) surgically separating said intercostal space;
  (c) inserting said heart massager through said intercostal space and guiding the heart-contacting member onto the ventricular region of said heart; and
  (d) periodically depressing and releasing the handle so that the heart's ventricles are alternately compressed and allowed to return to their non-compressed condition, the substantially upright handle imparting downward forces to the heart-contacting member during the periodic depressions.

2. A method of heart massage according to claim 1, wherein said incision is made in the fourth intercostal space.

3. A method of heart massage according to claim 1, wherein said incision is made in the intercostal space between the left nipple and the lateral border of the sternum.

4. A method of heart massage, the method comprising the steps of: employing a heart massager having a heart-contacting member with a heart-contacting surface which is at least partially concave and cushioning means comprising deformable material on said surface, said heart-contacting member being connected to a handle, the heart-contacting member having a plane tangential to at least a portion of the member's concave surface in a region where the handle is attached to the heart-contacting member, the handle being substantially upright with respect to the plane;

(a) making an incision in the skin in an intercostal space;
  (b) surgically separating said intercosial space;
  (c) inserting said heart massager through said intercostal space and guiding the heart-contacting member onto the ventricular region of said heart; and
  (d) periodically depressing and releasing the handle so that the heart's ventricles are alternately compressed and allowed to return to their non-compressed condition, the cushioning means providing a cushioning action for the heart as the substantially upright handle is depressed, the substantially upright handle imparting downward forces to the heart-contacting member during the periodic depressions.

5. A method of heart massage, the method comprising the steps of: employing a heart massager having a heart-contacting member with a heart-contacting surface which is at least partially concave, said heart-contacting member comprising a generally curved plate, said heart-contacting member being connected to a handle, the heart-contacting member having a plane tangential to the member's concave surface in a region where the handle is attached to the heart-contacting member, the handle being substantially upright with respect to the plane;

(a) making an incision in the skin in an intercostal space;
  (b) surgically separating said intercostal space;
  (c) inserting said heart massager through said intercostal space and guiding the heart-contacting member onto the ventricular region of said heart, the curved plate conforming to the surface of the heart's ventricular region; and
  (d) periodically depressing and releasing the handle so that the heart's ventricles are alternately compressed and allowed to return to their non-compressed condition, the substantially upright handle imparting downward forces to the heart-contacting member during the periodic depressions.

6. A method of heart massage, the method comprising the steps of: employing a heart massager having a heart-contacting member connected to a handle, the heart-contacting member having a heart-contacting surface and a circumferential sidewall supporting the surface, the sidewall being expandable and compressible, the heart-contacting surface and sidewall defining a substantially enclosed volume, the volume being less when the sidewall is compressed than when the sidewall is expanded, the handle being substantially rigid and having a longitudinal axis extending along its length;

(a) making an incision in the skin in an intercostal space;
  (b) surgically separating said intercostal space;
  (c) locating the ventricular region of the heart relative to said intercostal space;
  (d) inserting the heart massager through said intercostal space and guiding the heart-contacting member in its compressed condition onto the ventricular region;
  (e) expanding said sidewall of said heart-contacting member; and
  (f) periodically translating the rigid handle in a direction substantially along its longitudinal axis, the translation of the handle causing corresponding translation of the heart-contacting surface toward and away from the heart's surface so that the heart's ventricles are alternately compressed and allowed to return to their non-compressed condition, the translation of the handle imparting downward forces to the heart-contacting member through the circumferential sidewall.

7. A method of heart massage according to claim 6, wherein said incision is made in the fourth intercostal space.

8. A method of heart massage according to claim 6, wherein said incision is made in the intercostal space between the left nipple and the lateral border of the sternum.

9. A method of heart massage, the method comprising the steps of: employing a heart massager having a heart-contacting member connected to a handle, the heart-contacting member having a heart-contacting surface and a circumferential sidewall supporting the surface and extending longitudinally towards the handle, the sidewall being radially expandable and compressible, said sidewall having an outer diameter which is less than about one inch when the member is in a compressed state, said circumferential sidewall having a longitudinal axis, the handle being substantially rigid and having a longitudinal axis extending along its length, the longitudinal axis of the handle lying substantially along the axis of the circumferential sidewall;

(a) making an incision in the skin in an intercostal space;

(b) surgically separating said intercostal space;

(c) inserting said heart massager in its compressed condition through said intercostal space and guiding the heart-contacting member onto the ventricular region of said heart;

(d) radially expanding said sidewall of said heart-contacting member, the radially expanded sidewall being substantially bisected by the longitudinal axis of the handle; and (e) periodically translating the rigid handle in a direction substantially along its longitudinal axis, the translation of the handle causing corresponding translation of the heart-contacting surface toward and away from the heart's surface so that the heart's ventricles are alternately compressed and then allowed to return to its non-compressed condition, the translation of the handle imparting downward forces to the heart-contacting member through the radially expanded sidewall.

10. A method of heart massage according to claim 9, wherein said incision is made in the fourth intercostal space and is about one inch in length.

11. A method of heart massage according to claim 9, wherein said incision is made in the intercostal space between the left nipple and the lateral border of the sternum.

12. A method of heart massage, the method comprising the steps of: employing a heart massager having a heart-contacting member with a heart-contacting surface which is at least partially concave, said heart-contacting member being connected to a handle, the heart-contacting member having a plane tangential to the member's concave surface in a region where the handle is attached to the heart-contacting member, the handle being substantially upright with respect to the plane, the heart contacting surface having at least one electrode thereon in communication with an external heart monitoring device through an electrical connection path in the handle;

(a) making an incision in the skin in an intercostal space;

(b) surgically separating said intercostal space;

(c) inserting said heart massager through said intercostal space and guiding said heart-contacting member onto the ventricular region of said heart;

(d) periodically pressing and releasing the handle so that the heart's ventricles are alternately compressed and then allowed to return to their non-compressed condition, the substantially upright handle imparting downward forces to the heart-contacting member during the periodic depressions; and (e) transmitting electrical signals between the electrode and the external heart monitoring device through the electrical connection path in the handle while the surface of the heart-contacting member is contacting the heart.

13. A method of heart massage according to claim 12, wherein said incision is made in the fourth intercostal space.

14. A method of heart massage according to claim 12, wherein said incision is made in the intercostal space between the left nipple and the lateral border of the sternum.

15. A method of heart massage, the method comprising the steps of: employing a heart massager having a heart-contacting member with a heart-contacting surface which is at least partially concave, said heart-contacting member being connected to a handle which is substantially upright with respect to the surface of the heart-contacting member, the heart-contacting surface having an endoscope with a light source associated therewith and means for directing the light source to said heart-contacting member;

(a) making an incision in the skin in an intercostal space;

(b) surgically separating said intercostal space;

(c) inserting said heart massager through said intercostal space, and then, using said endoscope to guide said heart-contacting member onto the ventricular region of said heart; and (d) periodically pressing and releasing said handle so that the heart's ventricles are alternately compressed and allowed to return to their non-compressed condition, the substantially upright handle imparting downward forces to the heart-contacting member during the periodic depressions.

16. A method of heart massage according to claim 1, further comprising the step of monitoring the blood pressure of the heart during said pressing and releasing of said handle, said heart-contacting member being positioned during said pressing and releasing in a manner to increase said monitored blood pressure.

17. A method of heart massage according to claim 15, wherein said incision is made in the intercostal space between left nipple and the lateral border of the sternum.

18. A method of heart massage according to claim 12, wherein the heart contacting surface has an electrical signal sensor thereon and the electrical heart monitoring or controlling device is an electrocardiograph, step (e) comprising receiving electrocardiographic signals from the sensor.

19. A method of heart massage according to claim 12, wherein the heart contacting surface has an electrode thereon and the electrical heart monitoring or controlling device is a cardiac pacing device, step (e) comprising transmitting electrical signals from the device to the electrode.

20. A method of heart massage according to claim 12, wherein the heart contacting surface has electrodes thereon and the electrical heart monitoring or controlling device is a defibrillator, step (e) comprising transmitting electrical signals from the defibrillator to the electrodes.

21. A method of heart massage according to claim 12, wherein the heart contacting surface has a pressure sensor thereon and the electrical heart monitoring and controlling device is a compression pressure warning device, step (e) comprising receiving pressure signals from the sensor.

22. A method of heart massage, the method comprising the steps of: employing a heart massager having a heart-contacting member with a heart-contacting surface having an edge, said heart-contacting member being connected to a rigid handle, the handle having a longitudinal axis extending along its length, the longitudinal axis of the handle intersecting the heart-contacting surface at an angle substantially upright with respect to the contacting surface and at a location spaced from the edge;

(a) making an incision in the skin in an intercostal space;

(b) surgically separating said intercostal space;

(c) inserting said heart massager through said intercostal space and guiding the heart-contacting member onto the ventricular region of said heart; and (d) periodically translating the handle in a direction substantially along its longitudinal axis, the translation of the handle causing corresponding translation of the heart-contacting surface toward and away from the heart's surface so that the heart's ventricles are alternately compressed and allowed to return to their non-compressed condition.

23. A method of heart massage according to claim 22, wherein said incision is made in the fourth intercostal space.

24. A method of heart massage according to claim 22, wherein said incision is made in the intercostal space between the left nipple and the lateral border of the sternum.

25. A method of heart massage according to claim 22, further comprising the step of monitoring the blood pressure of the heart during said pressing and releasing of said handle, said heart-contacting member being positioned during said pressing and releasing in a manner to increase said monitored blood pressure.

26. A method of heart massage according to claim 22, wherein the heart-contacting member has a heart-contacting surface which is at least partially concave and includes cushioning means comprising deformable material on said surface, and during step (d), the cushioning means provides a cushioning action for the heart as the handle is depressed.

27. A method of heart massage according to claim 22, wherein the heart contacting member comprises a generally curved plate, and during step (c), the curved plate conforms to the surface of the heart's ventricular region.

28. A method of heart massage according to claim 22, wherein the heart-contacting member has a heart-contacting surface, said heart-contacting surface having at least one electrode thereon in communication with an external heart monitoring device through an electrical connection path in the handle, the method further comprising the step of:

(e) transmitting electrical signals between the electrode and the external heart monitoring device through the electrical connection path in the handle while the surface of the heart-contacting member is contacting the heart.

29. A method of heart massage according to claim 28, wherein the heart contacting surface has an electrical signal sensor thereon and the electrical heart monitoring or controlling device is an electrocardiograph, step (e) comprising receiving electrocardiographic signals from the sensor.

30. A method of heart massage according to claim 28, wherein the heart contacting surface has an electrode thereon and the electrical heart monitoring or controlling device is a cardiac pacing device, step (e) comprising transmitting electrical signals from the device to the electrode.

31. A method of heart massage according to claim 28, wherein the heart contacting surface has electrodes thereon and the electrical heart monitoring or controlling device is a defibrillator, step (e) comprising transmitting electrical signals from the defibrillator to the electrodes.

32. A method of heart massage according to claim 28, wherein the heart contacting surface has a pressure sensor thereon and the electrical heart monitoring and controlling device is a compression pressure warning device, step (e) comprising receiving pressure signals from the sensor.

33. A method of heart massage according to claim 22, wherein the heart-contacting member has an endoscope with a light source associated therewith and means for directing the light source to said heart-contacting member, step (c) further comprising using said endoscope to guide said heart-contacting member onto the ventricular region of said heart.

34. A method of heart massage, the method comprising the steps of: employing a heart massager having a heart-contacting member connected to a handle, the heart-contacting member having a heart-contacting surface and a circumferential sidewall supporting the surface, the sidewall being expandable and compressible, the heart-contacting surface and the sidewall defining a substantially enclosed voluble, the volume being less when the sidewall is compressed than when the sidewall is expanded;

(a) making an incision in the skin in an intercostal space;

(b) surgically separating said intercostal space;

(c) locating the ventricular region of the heart relative to said intercostal space;

(d) inserting the heart massager through said intercostal space and guiding the heart-contacting member in its compressed condition onto the ventricular region of said heart;

(e) expanding said sidewall of said heart-contacting member; and (f) periodically depressing and releasing the handle so that the heart's ventricles are alternately compressed and allowed to return to their non-compressed condition, the depression of the handle imparting downward forces to the heart-contacting member through the circumferential sidewall.

35. A method of heart massage according to claim 34, wherein said incision is made in the fourth intercostal space.

36. A method of heart massage according to claim 34, wherein said incision is made in the intercostal space between the left nipple and the lateral border of the sternum.

37. A method of heart massage, the method comprising the steps of: employing a heart massager having a heart-contacting member connected to a handle, the heart-contacting member having a heart-contacting surface and a circumferential sidewall supporting the surface, the sidewall being radially expandable and compressible, said sidewall having an outer diameter which is less than about one inch when the member is in a compressed state;

(a) making an incision in the skin in an intercostal space;

(b) surgically separating said intercostal space;

(c) inserting said heart massager in its compressed condition through said intercostal space and guiding the heart-contacting member onto the ventricular region of said heart;

(d) radially expanding said sidewall of said heart-contacting member; and (e) periodically depressing and releasing the handle so that the heart's ventricles are alternately compressed and then allowed to return to its non-compressed condition, the depression of the handle imparting downward forces to the heart-contacting member through the radially expanded sidewall.

38. A method of heart massage according to claim 37, wherein said incision is made in the fourth intercostal space and is about one inch in length.

39. A method of heart massage according to claim 37, wherein said incision is made in the intercostal space between the left nipple and the lateral border of the sternum.

40. A method of heart massage according to claims 1, 4, 5, 6, 9, 12, 15, 22, 34 and 37 wherein the pericardium remains intact when performing the steps of the method and the step of guiding the heart contacting member onto the ventricular region of the heart includes guiding the heart contacting member onto the outer surface of the pericardium.

* * * * *

UNITED STATES PATENT AND TRADEMARK OFFICE
CERTIFICATE OF CORRECTION

PATENT NO. : 5,484,391
DATED : Jan. 16, 1996
INVENTOR(S) : Robert F. Buckman, Jr., et al It is certified that error appears in the above-indentified patent and that said Letters Patent is hereby corrected as shown below:

On title page, add item [73]
    Assignee:   Temple University-Of The Commonwealth System of Higher Education Philadelphia, PA Signed and Sealed this Thirteenth Day of August, 1996

*Attest:*

BRUCE LEHMAN

*Attesting Officer*     *Commissioner of Patents and Trademarks*